(12) United States Patent
Beger et al.

(10) Patent No.: US 11,266,392 B2
(45) Date of Patent: Mar. 8, 2022

(54) STENT RETRACTOR/DISTRACTOR

(71) Applicant: Aesculap AG, Tuttlingen (DE)

(72) Inventors: Jens Beger, Tuttlingen (DE); Ulrike Pfeiffer, Muehlheim (DE); Richard Stacey, Oxford (GB); Thomas Cadoux-Hudson, Oxford (GB); Tobias Wäschle, Koenigsheim (DE); Christian Grimm, Tuttlingen (DE); Frank-Markus Storz, Tuttlingen (DE); Francis Kilian, Emmelshausen (DE)

(73) Assignee: AESCULAP AG, Tuttlingen (DE)

( * ) Notice: Subject to any disclaimer, the term of this patent is extended or adjusted under 35 U.S.C. 154(b) by 0 days.

(21) Appl. No.: 14/997,839

(22) Filed: Jan. 18, 2016

(65) Prior Publication Data
US 2016/0213500 A1 Jul. 28, 2016

(30) Foreign Application Priority Data

Jan. 22, 2015 (DE) .................. 102015100932.3

(51) Int. Cl.
*A61B 17/02* (2006.01)

(52) U.S. Cl.
CPC ........ *A61B 17/0218* (2013.01); *A61B 17/025* (2013.01); *A61B 2017/0225* (2013.01); *A61B 2017/0256* (2013.01)

(58) Field of Classification Search
CPC ...... A61F 2250/0018; A61F 2250/0048; A61F 2002/825; A61F 2002/91583; A61F 2220/0016; A61F 2/962; A61F 2/82; A61F 2250/001; A61F 2/93; A61F 2210/0004; A61F 2002/9511; A61B 17/0218; A61B 17/025; A61B 2017/0225; A61B 2017/0256; A61B 2250/0018; A61B 17/3468; A61B 17/7091; A61B 17/7076; A61B 17/02

(Continued)

(56) References Cited

U.S. PATENT DOCUMENTS

| 5,035,706 A | 7/1991 | Giantureo et al. |
| 5,383,887 A * | 1/1995 | Nadal ............... A61F 2/01 |
| | | 606/198 |

(Continued)

FOREIGN PATENT DOCUMENTS

| CN | 1187115 A | 7/1998 |
| CN | 102413793 A | 4/2012 |

(Continued)

OTHER PUBLICATIONS

German Search Report dated Nov. 4, 2015 for German Application No. 10 2015 100 932.3, including partial English language translation.

(Continued)

*Primary Examiner* — Brian E Pellegrino

(57) ABSTRACT

A stent retractor/distractor includes a radially flexibly enlargeable, pipe-shaped sheath which is divided up in the circumferential direction in at least two sections, namely one stiffening section and one enlarging section with differing radial flexibilities, which are connected with each other in one piece of material. The stent retractor/distractor defined in that way is made on the whole by a laser or water jet cutting procedure, preferably from a pipe blank.

10 Claims, 9 Drawing Sheets

Figure 1:
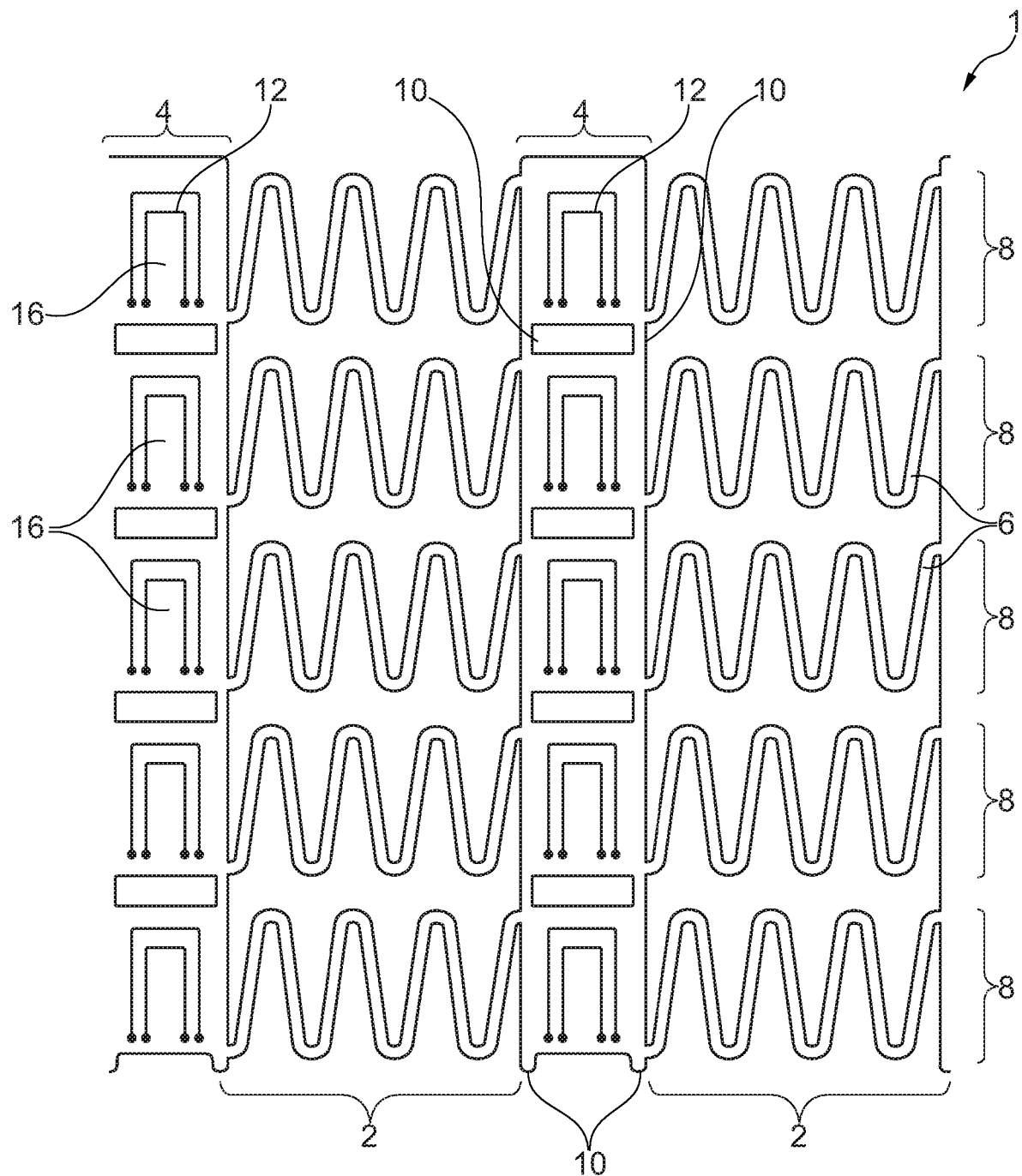

(58) Field of Classification Search
USPC .......................................................... 623/1.17
See application file for complete search history.

(56) References Cited

U.S. PATENT DOCUMENTS

| | | | |
|---|---|---|---|
| 5,800,515 A * | 9/1998 | Nadal | A61F 2/07 623/1.15 |
| 6,017,365 A | 1/2000 | Von Oepen | |
| 6,077,297 A | 6/2000 | Robinson et al. | |
| 6,113,628 A * | 9/2000 | Borghi | A61F 2/856 600/36 |
| 6,187,000 B1 | 2/2001 | Davison | |
| 8,372,131 B2 | 2/2013 | Hestad | |
| 8,403,978 B2 | 3/2013 | Schlun et al. | |
| 2002/0087163 A1 * | 7/2002 | Dixon | A61B 17/025 606/90 |
| 2005/0125053 A1 | 6/2005 | Yachia | |
| 2006/0173529 A1 | 8/2006 | Blank | |
| 2006/0287706 A1 | 12/2006 | Olsen et al. | |
| 2007/0067012 A1 | 3/2007 | George et al. | |
| 2007/0219613 A1 | 9/2007 | Kao et al. | |
| 2008/0195190 A1 | 8/2008 | Bland et al. | |
| 2008/0300665 A1 | 12/2008 | Lootz | |
| 2009/0024203 A1 | 1/2009 | Hestad et al. | |
| 2010/0256741 A1 | 10/2010 | Hansen | |
| 2010/0312189 A1 | 12/2010 | Shelton | |
| 2011/0054260 A1 * | 3/2011 | Albrecht | A61B 17/0218 600/208 |
| 2011/0144687 A1 | 6/2011 | Kleiner | |
| 2012/0065722 A1 * | 3/2012 | Pacetti | A61F 2/915 623/1.15 |
| 2012/0083868 A1 | 4/2012 | Shrivastava et al. | |
| 2013/0066158 A1 * | 3/2013 | Rodriguez | A61B 1/32 600/208 |
| 2014/0236282 A1 | 8/2014 | Andreas et al. | |
| 2014/0288629 A1 | 9/2014 | Amendt et al. | |
| 2014/0364935 A1 | 12/2014 | Eli et al. | |
| 2016/0022448 A1 * | 1/2016 | Tobis | A61F 2/848 623/1.16 |
| 2016/0213500 A1 | 7/2016 | Beger et al. | |
| 2019/0343504 A1 | 11/2019 | Beger et al. | |

FOREIGN PATENT DOCUMENTS

| | | | |
|---|---|---|---|
| CN | 103153214 A | 6/2013 | |
| DE | 29708879 U1 | 7/1997 | |
| DE | 10103000 A1 | 8/2002 | |
| DE | 102007025921 | 12/2008 | |
| DE | 202011107781 U1 | 12/2011 | |
| DE | 102015100933 A1 | 7/2016 | |
| EP | 3181096 A1 | 6/2017 | |
| JP | 03133446 A | 6/1991 | |
| JP | 07265339 A | 10/1995 | |
| JP | 11507567 A | 7/1999 | |
| WO | WO-9421196 A2 * | 9/1994 | A61F 2/93 |
| WO | 9937245 | 7/1999 | |
| WO | 2013106585 A1 | 7/2013 | |
| WO | 2014022094 | 2/2014 | |
| WO | 2014141239 A1 | 9/2014 | |

OTHER PUBLICATIONS

Roche Lexikon Medizin, 5. Auflage, Urban & Fischer 2003, Definition: "Distraktor", "Stent" and "Wundsperrer", including English language translation (pp. 1-3).
Japanese Notification of Reason for Rejection for Japanese Application No. 2016-010829, dated Dec. 3, 2019 with translation, 6 pages.
Chinese Office Action for Chinese Application No. 201610044869. 5, dated Jul. 31, 2019, with translation, 18 pages.
German Search Report for German Application No. 10 2016 118 605.8, dated May 18, 2017, 12 pages.
Chinese Office Action received in Application No. 201780060843.2 dated Nov. 2, 2020, 13 pages.
Chinese Search Report received in Application No. 2017800608432 dated Oct. 20, 2020, 3 pages.
International Search Report for International Application No. PCT/EP2017/074509, dated Dec. 15, 2017, 5 pages.
Written Opinion received in International Application No. PCT/EP2017/074509, dated Dec. 15, 2017, 13 pages.

* cited by examiner

STENT RETRACTOR/DISTRACTOR

RELATED APPLICATION(S)

The present application is related to and claims the benefit of priority of German Application No. 10 2015 100 932.3, filed Jan. 22, 2015, the content of which is incorporated by reference herein in its entirety.

FIELD

The present invention concerns a stent-like retractor/distractor, and in particular, a stent that is adapted to be used as a retractor and/or as a distractor (retractor and/or distractor in the form of a stent).

BACKGROUND

Generally, a distractor is a surgical instrument or device for distraction. The controlled spreading and possibly permanent apposition of bones in the spreading zone is referred to as distraction in this connection. In general, distractors are used in accident surgery, orthopaedics and jaw surgery for the extension treatment of bones.

A retractor, however, is a surgical instrument used to keep an operating area/incision open.

This instrument is inserted in the operating area from outside the patient and the spreading elements are spaced apart from each other. This pushes connective and/or muscle tissues apart and extends the operating area. The required extension forces are applied either extracorporeally by means of support arms that may be fixed on the operating table or intracorporeally by means of spring and/or supporting elements which apply force to each of the spreading elements.

For example, U.S. Pat. No. 6,187,000 B1 discloses a retractor with an expandable, distal end. Here, a kind of foil made of non-rusting metal is rolled up into a pipe/funnel, whereby the foil edges that adjoin to each other and/or overlap are riveted to each other. Here a first, axial end-side rivet constitutes a swing hinge, whereas a second, axially spaced end-side rivet is guided in a motion link shaped into the foil and running around the circumference with the foil rolled up in order to increase or reduce the diameter of the foil roll by sections by means of pivoting around the first rivet in that way. In that way, a cylinder shape and a funnel shape can be created.

From U.S. Pat. No. 8,372,131 B1, another structure for a stent retractor of the type in hand is known. This structure provides for the arrangement of a stent pipe or hose, consisting of a material processed into a homogeneous wire mesh, preferably with memory characteristics, whereby the wire mesh is coated with a fluid-tight membrane, for example made of PTFE, on the inside and/or the outside. First, the stent hose is fixed on a dilation set, consisting of a trocar shaft that is surrounded by a dilation balloon and that has, at its distal end, a kind of bone anchor in the shape of a single, centrally arranged nail or a bone screw.

For the intracorporeal placement of the stent retractor, the trocar shaft is introduced in the patient's body and anchored to one of the patient's bones (e.g. dorsal vertebra) by means of the nail or the screw. Then the dilation balloon is inflated, as a result of which the stent retractor expands radially and pushes the surrounding patient tissue radially apart in a steady manner in the process. After loosening of the bone anchor and retracting of the trocar shaft, leaving behind the expanded stent retractor, a patient access with an access diameter remains for the performing of surgery, preferably by means of minimally invasive surgical instruments, which can be introduced in the canal defined by the stent retractor.

Finally, a textile structure with separate support elements for the formation of a retraction device is generally known from WO 2014/022094 A1. According to that, a braided fabric shaped into a hose is pressed radially to the outside by means of a kind of separate supporting frame in order to apply an enlarging force to the surrounding patient tissue. Furthermore, the support frame has a number of bars that radially penetrate the braided fabric to the outside, and these bars temporarily implant themselves in the patient tissue and so keep the structure in an axial position on the patient's body.

However, it has become apparent that the above-mentioned retractor systems have a large number of components on the whole and that it is therefore relatively expensive to produce them. Consequently, they cannot be used as disposable items or only to a limited degree.

In addition, their area of application is limited exclusively to the retractor function. So if surgical operations are planned which, for example, require bone distraction, further special distraction instruments are necessary for that, which have to be introduced in the patient through the access canal created with the stent retractor and placed accordingly.

SUMMARY

In view of the above-mentioned state of the art, the purpose of the invention in hand is to provide a generic stent (retractor/distractor) and/or stent with retractor function and/or distractor function that is suitable for and/or designed as a disposable item.

In addition, a preferred objective of the invention in hand is to extend the area of application of the retractor according to the invention, preferably for an additional/alternative use as a distractor.

The above-mentioned problems and objectives are solved/achieved according to the invention with a stent retractor/distractor and/or stent with retractor function and/or distractor function (stent, adapted to be used as a retractor and/or distractor).

According to a first aspect of the invention in hand, a stent is proposed accordingly which is adapted for use as a retractor and distractor. For that purpose, the stent has a radially flexibly enlargeable, tube-shaped wall structure which is divided up, seen in the circumferential direction, in at least two sections with (radial) flexibilities that differ from each other. The stent is made of a single piece (of material). The division of the wall structure according to the invention in sections with a greater and lesser flexibility gives the stent the property enabling it to be deformed in the radial direction in any way (e.g. round, oval, etc.) and still to maintain a sufficient stiffness to keep tissue in a pressed-apart state. In that way, a minimally invasive access, for example in the form of a lumbar, thoracic and/or cervical spinal column access, can be created. Cranial applications are possible as well.

The enlarging sections serve to enable changing of the diameter of the stent, whereas the stiffening sections increase the stability of the stent as regards external radial forces in at least certain radial directions. This makes it possible to use the stent, as an alternative or in addition to its retraction function, also as a distractor instrument because its resistance forces that can be achieved on principle in particular through the stiffening sections against radially acting compression forces can be sufficient to keep bones apart.

The preferably single-piece (material) design of the stent enables simply and fast manufacturing, for example by means of laser or water cutting of metal sheets. This allows for the economically feasible realization of a single-use concept.

Preferably, the wall structure (the sheath) of the stent is divided up in four sections in the circumferential direction, two of which are designed with basically and/or approximately the same flexibility as stiffening sections and are in addition formed with basically and/or approximately the same flexibility as enlarging sections, for which purpose the two stiffening sections have a greater stiffness than the two enlarging sections at least in the circumferential direction and/or in the axial direction. As a result of this further development, the stent can be enlarged with simple aids, such as a dilation balloon, a speculum or a Langenbeck hook, preferably uniformly (symmetrically) or also ovally when a surgeon intends to do that. For this purpose in particular, the two sections with the same flexibility in each case may also be arranged diametrically opposite each other.

According to a preferred, possibly independently claimable embodiment of the invention in hand, the stiffening sections are formed or fitted with carrier and/or fixing structures for additional components. These fixing structures can be formed preferably by means of punching out or cutting out of the stiffening sections. For that purpose, in particular, the stiffening sections may consist of a closed sheet metal plate each, in which, for example, (full-length) preferably U-shaped slits are worked (cut), as a result of which lugs or tongues can be formed. If these are bent radially to the outside, open, groove-shaped indentations are created, preferably in the axial direction, in which additional (separate) components, such as a sealing foil, can be hooked or pushed, which surrounds the stent structure (the sheath) inside and/or outside with a basically loose attachment and so creates a fluid seal and/or serves as tissue protection.

According to a preferred, possibly independently claimable embodiment of the invention in hand, a lacing device, preferably in the form of a puling rope or a shoestring, can be provided as an additional component, which is threaded in the lugs (now preferably formed as eyelets) in such a way that the stent retractor is radially compressed during a lacing process, preferably with shortening of the effective length of the pulling rope.

According to a preferred, possibly separately claimable embodiment of the invention in hand, two bone anchoring elements, preferably in the form of nails or distraction screws, can be provided as additional components furthermore (in combination with or independently of the components already mentioned above), which are introduced diametrically to each other in the lugs (preferably formed as eyelets as of now) axially in such a way that they align themselves on the inside or outside of the sheath of the stent. When these bone anchoring elements are inserted, for example, in two adjacent vertebrae, distraction forces can be applied to the vertebrae when the stent is radially enlarged accordingly. As the stent according to the invention has the above-mentioned stiffening sections, the achievable distraction forces are so great that the bones (vertebrae) remain pressed apart without further (additional) distraction instruments. In this respect, the stent according to the invention can be used as a retractor and/or as a distractor system.

According to a preferred, possibly independently claimable embodiment of the invention, it is envisaged that the enlarging sections each consist of a number of axially distanced, preferably elastically or plastically deformable expansion elements which are preferably formed with an accordion wire extending in the circumferential direction. As a result of that, the wall structure of the stent can, in particular in the area of the enlarging sections, be created by means of punching or cutting, preferably laser or water cutting, for example from a (closed) pipe profile, which can be deburred in addition later on. As a result, production is easy and cost-efficient and consequently suitable for "single-use" products on the whole.

According to a preferred, possibly independently claimable embodiment of the invention, it is furthermore envisaged that the stent is divided up in the axial direction in a number of (circular) segments which have circumferentially spaced, internal stiffening and enlarging sections in each case according to the description above, whereby the segments are connected with each other by means of axial connecting elements/strips with preferably greater stiffness, which furthermore preferably constitute predetermined breaking points for segment-wise shortening of the length. This design ensures that the stent basically only widens radially when an inside pressure is applied. Furthermore, the length of the stent can easily be adapted to its intended site of use on the patient's body.

BRIEF DESCRIPTION OF THE DRAWING FIGURES

Figure 2A:
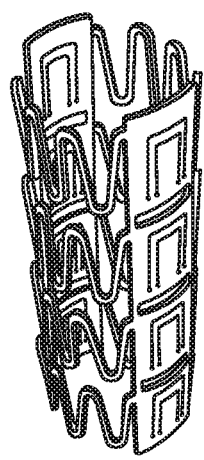
Figure 2B:
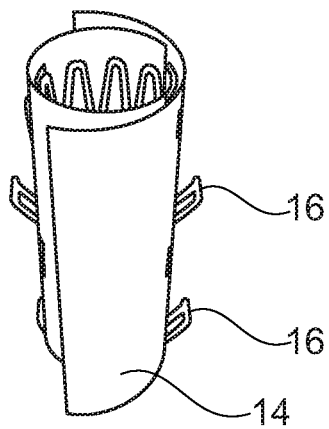
Figure 2C:
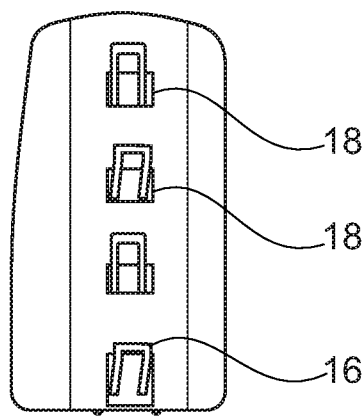
Figure 3:
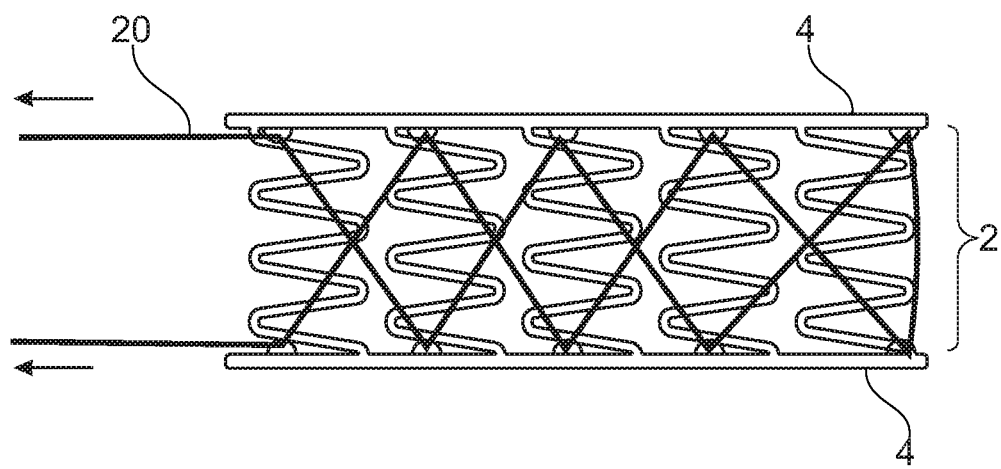
Figure 4A:
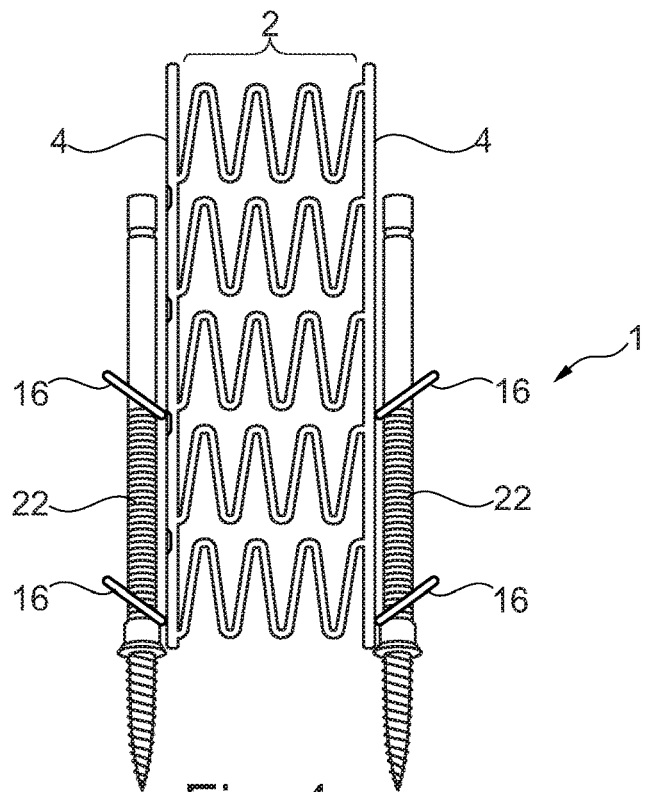
Figure 4B:
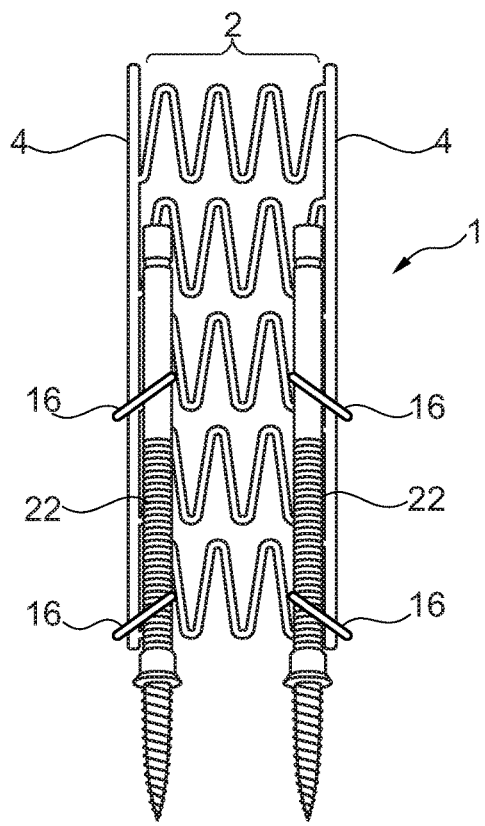
Figure 5:
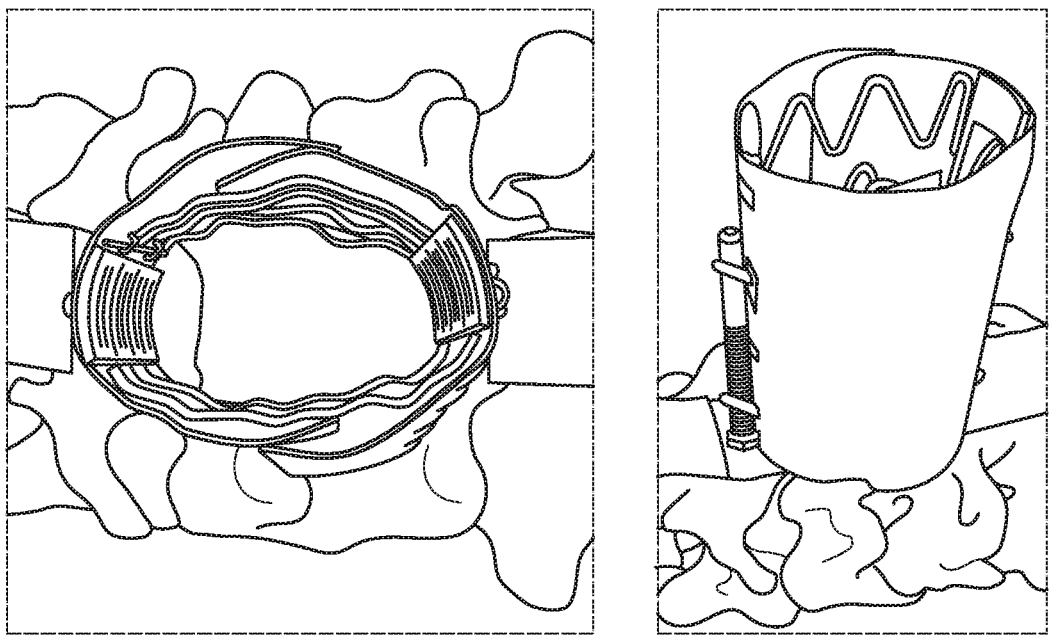
Figure 5:
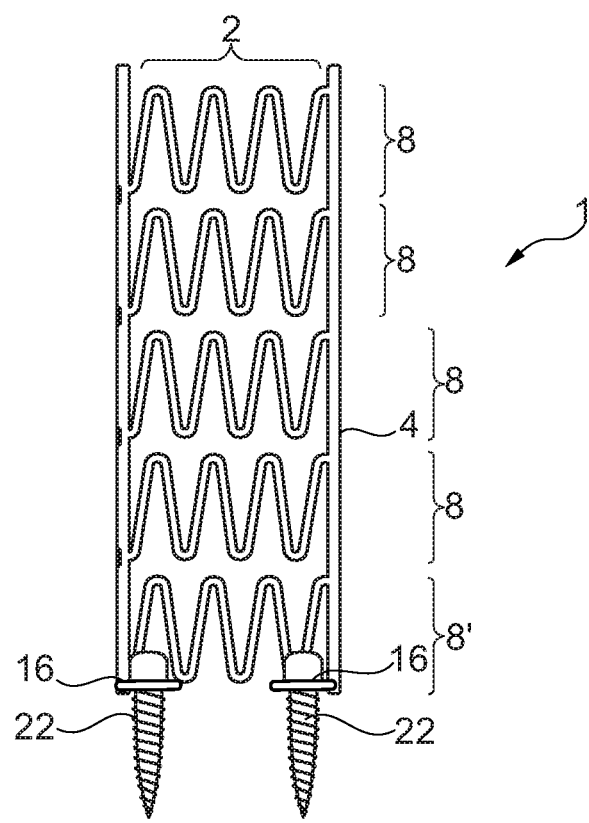
Figure 6:
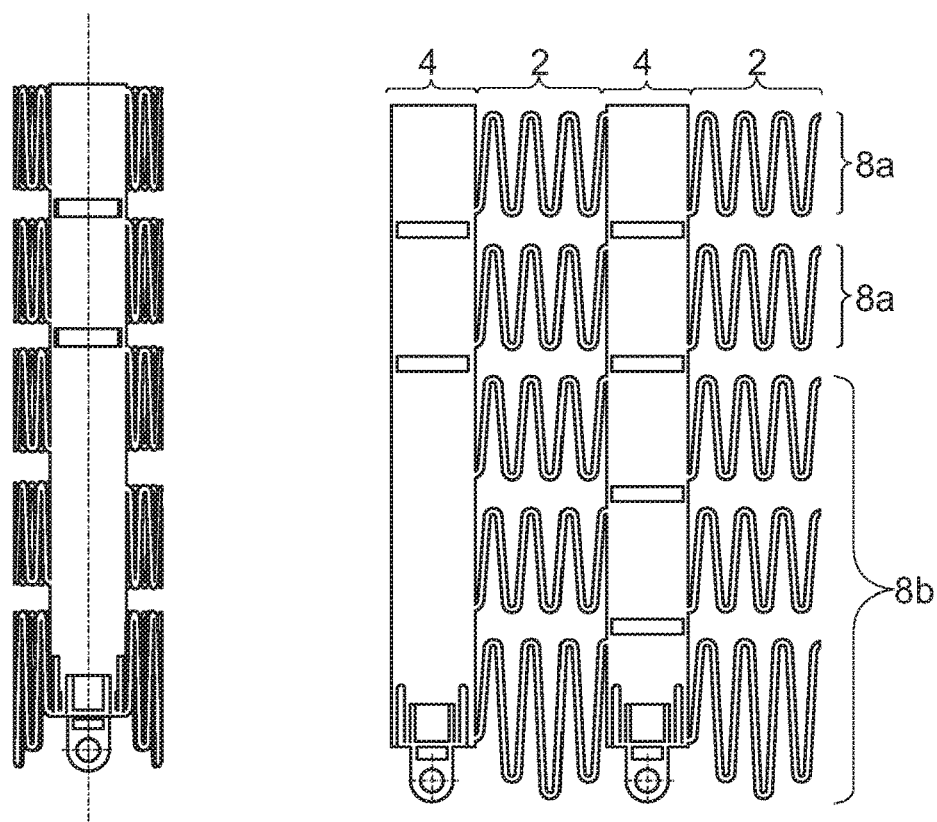
Figure 7:
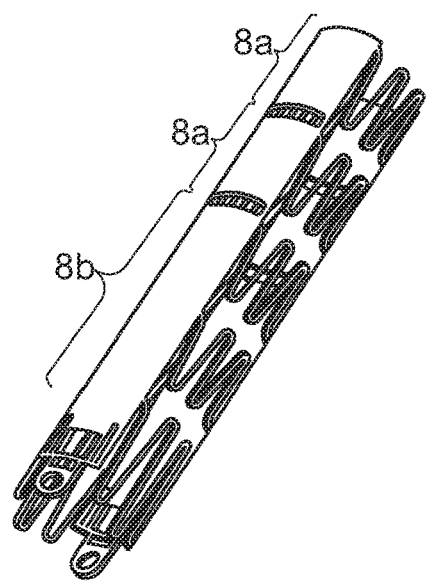
Figure 8:
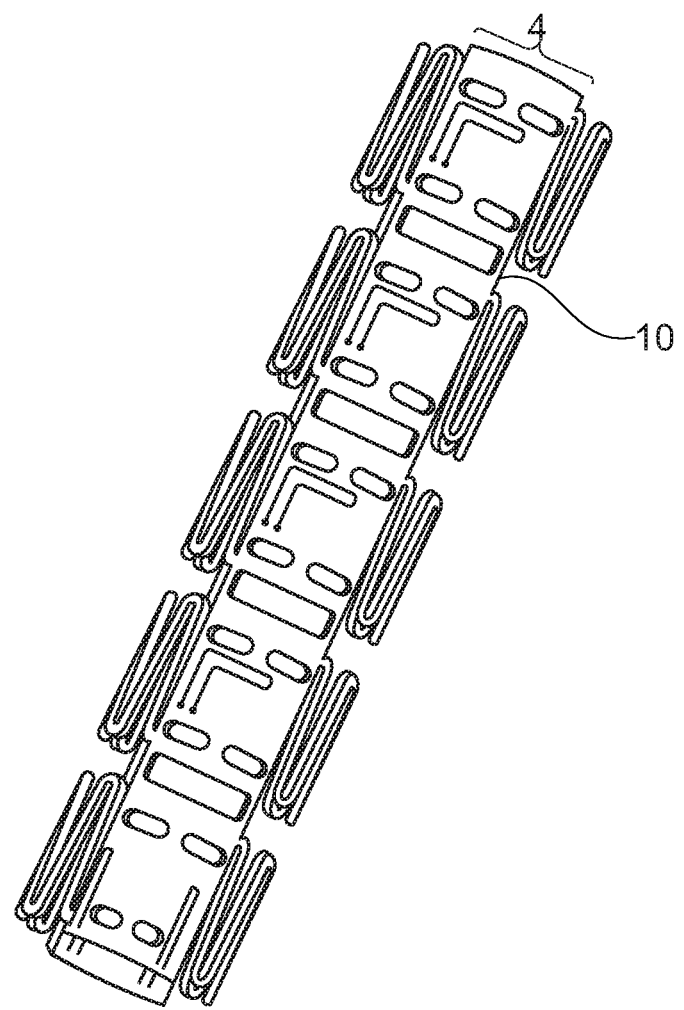
Figure 9:
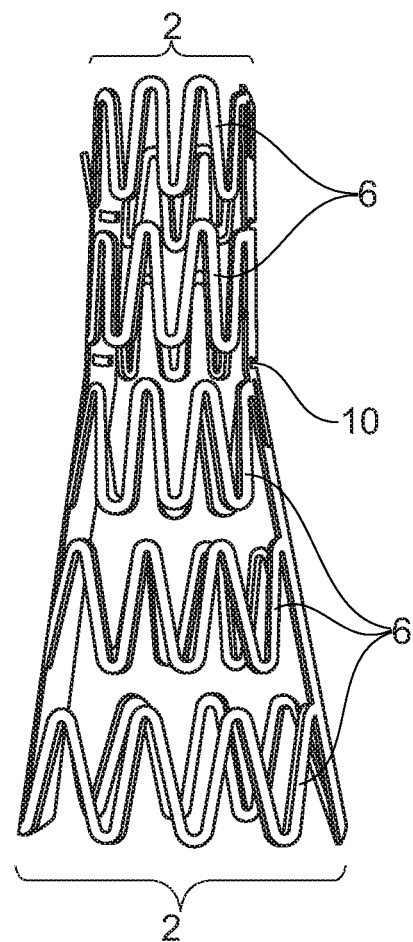
Figure 10A:
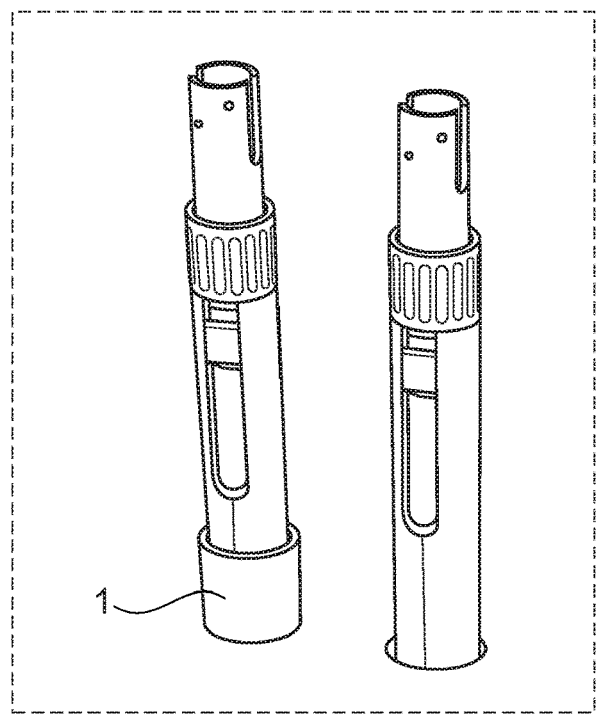
Figure 10B:
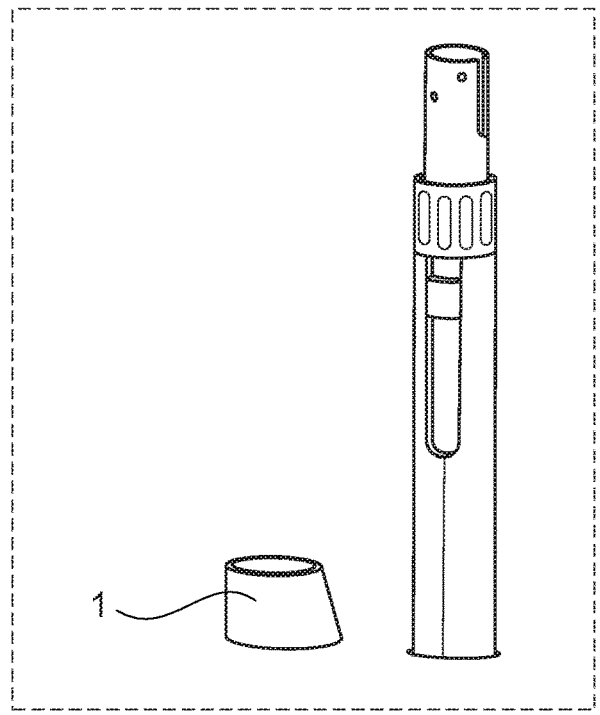

Below, the invention is explained in more detail based on preferred exemplary embodiments with reference to the accompanying figures, of which:

FIG. 1 shows the realization of a wall structure of a stent according to a first preferred exemplary embodiment of the invention in hand, FIG. 2a-c show the pipe or hose-shaped stent according to the invention according to FIG. 1 as pre-product and equipped with a separate fluid seal wall, FIG. 3 shows the pipe- or hose-shaped stent according to the invention with a separate lacing device as an alternative or in addition to the fluid seal wall, FIG. 4a-b show the pipe- or hose-shaped stent according to the invention, equipped with separate bone anchoring elements arranged on the outside of the stent as an alternative or in addition to the fluid seal wall and/or lacing device, FIG. 5 shows the pipe- or hose-shaped stent according to the invention, equipped with separate bone anchoring elements arranged inside the stent as an alternative or in addition to the fluid seal wall and/or the lacing device, FIG. 6 shows the realization of a wall structure of a stent according to a second, preferred exemplary embodiment of the invention in hand, FIG. 7 shows the pipe- or hose-shaped stent according to the invention according to FIG. 6 as pre-product FIG. 8 shows the pipe- or hose-shaped stent according to the invention according to FIG. 6, in which the stiffening sections/elements are equipped and/or formed with selected or selectable functionalities, FIG. 9 shows the pipe- or hose-shaped stent according to the invention according to FIG. 6 with section-wise enlarged diameter for achieving a section-wise funnel shape, in particular in an area with axially lengthened stiffening sections/elements and FIG. 10a-b show two functional diagrams for the visual representation of a possible stent application by means of a pedicle screw system already known from the state of the art.

DETAILED DESCRIPTION OF EMBODIMENTS

According to FIGS. 1 and 2a, the wall structure of a stent retractor-distractor 1 according to a first preferred exemplary embodiment of the invention in hand consists, seen in the circumferential direction, of two circumferential sections with a lesser stiffness 2 (hereinafter referred to as enlarging sections/elements) and two circumferential sections with a comparably greater stiffness 4 (hereinafter referred to as stiffening sections/elements) that are arranged alternately to each other in the circumferential direction and linearly in the axial direction.

In principle, stent 1 according to the invention has a pipe- or hose shape, whereby the circumferential sections with identical/similar stiffnesses are located diametrically opposite to each other. Furthermore, stent 1 is formed in one piece of material, i.e. the individual circumferential sections are connected with each other in a single piece of material.

The comparably thin-walled stent pipe (approx. 0.5 to 1.5 mm) is preferably divided up in the above-mentioned circumferential sections by means of laser cutting or water jet cutting. However, it is to be pointed out that other processing methods such as punching or cutting can also be used to produce the wall structure that will be described below. Depending on the requirements and the intended purpose/site of use, the initial diameter (inside diameter of the stent pipe in construction position, i.e. not enlarged) can be in a range of 10-30 mm, for example.

Basically, stent 1 has a wall structure taken over from a standard vascular stent (Coroflex) in outline. This means that stent 1 consists, at least in the area of its enlarging sections (enlarging elements) 2 of a number of axially spaced, preferably parallel-running straps 6, which extend in the circumferential direction in the shape of a snake or accordion and so constitute flexible enlarging reserves in the radial direction in the area of their accordion shape.

In order to increase stability, the stiffer circumferential sections (stiffening sections) 4 are arranged, seen in the circumferential direction, (alternately) between the two enlarging sections 2 in each case. The stiffening sections (stiffening elements) 4 are constituted by basically closed, preferably rectangular plate sections, the basic shape of which is, seen in the axial direction, curved like a tub or trough and which are designed for not or only slightly enlarging radially. The stiffening sections 4 are also used in order to create fixing structures for additional separate extension elements (fluid-tight sheathing, tissue protection, bone anchor, lacing device, etc.) as it is described below. Here, the objective is to integrate as many functions as possible in the geometry of the wall structure.

As can be gathered furthermore from FIGS. 1 and 2a, the stent 1 according to the invention consists of several axially spaced/separate (circular) segments 8, each also consisting of the four circumferential sections as described above, whereby the circular/axial segments 8 are connected with each other by means of strips 10 (in one piece of material). The advantage of this segmental structure is that in case of a radial enlargement of the stent diameter, its axial length basically remains the same because only the individual segments 8 are widened radially. Furthermore, the connecting strips 10 can easily be disconnected with cutting pliers or scissors or the strips 10 are designed as predetermined breaking points, which enables a length adjustment of stent 1 during surgery.

In the area of the stiffening sections 4, the plate-shaped stent wall is fitted segment-wise with U-shaped, circumferential through slits 12, as a result of which lugs or tongues 16 can be designed, which can be bent up radially to the inside or the outside. This produces notches/hooks that are open to one side in the axial direction which serve as fixing elements for separate attachment or additional components.

According to FIG. 2b, 2c, for example, two sealing pans 14 that partly overlap, for example made of Teflon, are mounted in the hooks 16, which surround the external circumferential side of the stent basically fluid-tight. For that purpose, each (plate-shaped) sealing pan 14 has a number of recesses 18, in which the hooks 16 fasten and so hold the sealing pans 14. As the hooks 16 are formed in areas of the stiffening sections 4 in which the two pans 14 rest flat on the stent wall in each case, only minor leaks develop there, which have no major effect on the fluid retention function and/or the tissue retention function of the pans 14.

As can be gathered from FIG. 2c in particular, the lugs/tongues/hooks 16 preferably have an eyelet function. In other words, the lugs/tongues/hooks 16 are not flat, but bow-shaped, and so create an eyelet that is or can be bent to the stent wall to the outside or the inside in each case.

FIG. 3 shows a first option for the use of this eyelet function. In this case, the enlarging sections 2 have an inherent elasticity, i.e. the active diameter of stent 1 can be reduced against the spring force of the enlarging sections 2, and so the enlarging sections 2 can be pre-tensioned spring-loaded. When stent 1 is released then, the enlarging sections 2 widen to their original stent diameter (construction position) again.

As an option for the radial pre-tensioning of stent 1 in that manner, a lacing device 20 roughly based on the principle of a corset lacing is provided. Here, a pulling rope or wire of the lacing device 20 is threaded though the eyelets 16, for example in a crosswise arrangement. As soon as the two free ends of the pulling rope are tightened, the active length of the pulling rope between the eyelets 16 shortens, which makes stent 1 contract radially. When the pulling rope is released, stent 1 again spring-elastically widens to its original diameter.

In order to provide this option, the lugs/tongues/eyelets 16 are radially bent to the inside in this case. Then the lugs/tongues/eyelets 16 bent to the inside are no longer available for hooking in a fluid seal according to FIG. 2a, 2b. In order to enable the simultaneous, optional use of both attachment parts in spite of that, it is possible to bend only a selected number of axially spaced lugs/tongues/eyelets 16 radially to the inside and the remaining number radially to the outside.

According to FIG. 4a, a number of eyelet-shaped lugs/tongues 16 are radially bent to the outside, whereby on both stiffening sections 4, bone anchors 22 in the form of nails or threaded bolts are axially plugged in the bent lugs/tongues 16 on the outside. In contrast to this, however, it is also possible to bend a number of eyelet-shaped lugs/tongues 16 radially to the inside and to use bone anchors 22 in the form of nails or threaded bolts on both stiffening sections 4 on the inside, as this is shown as an alternative in FIG. 4b. In both cases, the bone anchors/screws 22 can be introduced in two bones (e.g. vertebrae) to be distanced from each other, and that in a diameter-reduced state of stent 1. If it is then radially enlarged—for example spring-elastically by means of a suitable pre-tensioning of the enlarging sections 2 or by means of plastic deformation of the enlarging sections 2, the spring-elastic enlargement force is transmitted to the two bones and puts them at a distance from each other. In particular because of the stiffening sections 4, stent 1 is rigid enough in order to keep the bones and possibly also the surrounding tissue at the pre-determined distance. This means that in this case, stent 1 does not only assume the retraction function according to the description above for the creation of a surgery access, in particular for minimally invasive instruments, but simultaneously or alternatively the distractor function for the spacing of two (adjacent) bones (vertebrae) and/or positioning of them at a distance.

It has to be pointed out that the function of stent 1 also strongly depends on the shape of the bone anchors 22 and/or can be supported by it. In that way, for example, in the embodiment according to FIGS. 4a and 4b, long threaded bolts are used, which extend across almost the entire stent length laterally on stent 1. As a result of that, stent 1 is also supported regarding its retractor function by means of the (stabilizing) bone screws across almost its entire axial length, whereby the diameter of the surgery access, however, now depends on the scope of distraction.

The embodiment according to FIG. 5, on the contrary, involves that a bone screw 22 with screw shaft and short screw head (i.e. without bolt shaft) is inserted in the end-side eyelet-shaped lugs 16 in each case. In this case, the distractor force is mostly applied by the axial segment 8' of stent 1 closest to the bones, whereas the retractor function of stent 1 is performed at least partially uncoupled by the remaining segments 8 of stent 1. In this case, the radial enlargement of segment 8' closest to the bones can be different from the radial enlargement of the remaining segments 8 (e.g. can be smaller or greater).

Here it is to be pointed out that the radial enlargement of stent 1 does not necessarily have to be achieved through the inherent elasticity of the enlarging sections 2 in particular. As an alternative to that, there is the option of a plastic deformation of the enlarging sections 2. In this case, stent 1 can first be (plastically) compressed after laser or water jet cutting to the outer diameter of an uninflated dilation balloon per se known from the state of the art. For this purpose, it is manufactured with a mean diameter and then radially compressed to the dilution balloon diameter. This procedure is useful for the retraction function in particular in order to optimise the ratio of minimum diameter to maximum spreading. This means that when the dilation balloon is inflated, stent 1 expands from its compressed position beyond its construction position into its maximum radial spreading without over-stretching the enlarging sections 2 in the process.

Steel, titanium or plastic can be used as material for stent 1 according to the invention, whereby a plastic part is preferably produced by means of die casting. In addition, stent 1 can be deburred after cutting of the wall profiles, for example by means of electro polishing. In order to improve furthermore the light reflection characteristics, for example with microscope applications, the surface of the remaining structures can also be matted or coated.

As already indicated above, different instruments and methods can be provided for plastic (not elastic) deformation. By means of the above-mentioned, pre-fixed balloon, the retractor/distractor 1 according to the invention can be enlarged hydraulically or pneumatically like on a vascular stent. Furthermore, a speculum known per se, which can create an oval opening, for example, has proven to be a simple procedure. Depending on the design of the speculum, stent 1 can be shaped (plastically) in any way. Depending on how the pivot point of the speculum is positioned relative to stent 1, a funnel-shaped opening, distal or proximal, is also possible.

Two wound hooks, e.g. Langenbeck hooks of a known construction type, can be used as further simple (plastic) spreading options. When these are supported against each other, a distal funnel-shaped spreading of stent 1 is possible as well. As the easiest option, stent 1 can also be (plastically) spread and shaped with the fingers.

Stent 1 can be destroyed for removal. It can be made smaller and then removed simply by compressing it. In particular for the case that during the enlarging process, a (distal) funnel-shaped structure was created, it is conceivable that for example, stent 1 is compressed again by means of compression pliers that grip in the stent structure. By means of rotational moments, the stent structure may possibly also be folded (twisted). Finally, the above-mentioned lacing device 20 provides an option for the plastic/elastic re-compression of the plastically enlarged stent 1. So the pulling rope/thread that is threaded, similarly to a shoelace, on both stiffening sections 4 in the eyelets 16 formed there, can be shortened with its free ends in order to radially compress stent 1 in that way.

In particular for cervical applications, it is advantageous when the distraction function that is otherwise performed by means of an additional distractor is integrated in the stent (retractor/distractor) 1 as it was already described above. For that purpose, existing Caspar distraction screws can serve as bone anchors 22. The anchoring points for the screws 22 are created by means of the eyelet-shaped lugs 16 which were worked in the laser structure and then bent outwards. With this method, first the screws 22 are placed and then the stent (retractor/distractor) 1 is threaded on the screw shafts or screw heads. An additional axial securing of stent 1 according to the invention should be formed in the process. This can be achieved, for example, by means of a clamp (not shown in more detail) which braces stent 1 with the screw shaft 22.

For minimally invasive cervical accesses, it has been shown that fixing inside the stent (retractor/distractor) 1 is more advantageous than on its outside. For this purpose, first the stent (retractor/distractor) 1 is placed, possibly even spread until the bone entry points of the fixing screws are in the middle of the cervical vertebrae, and the fixing screws are screwed in afterwards. The advantage of this procedure is that the screw 22 that was already screwed in assumes the axial securing of stent 1 at the same time. It is also conceivable that the screws 22 have already been pre-fixed to the stent (retractor/distractor) 1 before it is placed in the surgical opening.

When the stent (retractor/distractor) 1 is fixed with the bone anchors 22 (distraction screws) after placement, the stent (retractor/distractor) 1 can be sequentially repositioned by loosening the screws with a multi-segmental approach. An originally mono-segmental access can also be changed into a multi-segmental access by loosening a screw 22 and subsequent retraction.

With a lumbar concept, stent 1 does not necessarily have to be fixed. An integrated distraction function is also more difficult to realise because of the greater forces. However, a great advantage is, with a percutaneous procedure with pedicle screws, the simultaneous use of a caudal access for decompression and introduction of an inter-vertebral implant.

In order to achieve alignment of the stent (retractor/distractor) 1 in the muscle tissue, it can be useful to use an anchoring element 22 as fixing point. This may be, for example, a pin, a K-wire or the pedicle screw itself. For example, the pedicle screw can be fixed caudally on the stent wall. This can be done by means of an additional component (e.g. fixing cap) which is put on the screw head and fixed on the stent (retractor/distractor) 1.

For the protection of soft tissue structures, such as blood vessels, nerves and muscles, it may be necessary that the stent (retractor/distractor) 1 is fitted with the protective cover 14. This is in particular necessary for the cervical application. Foils that are also connected with the stent (retractor/distractor) 1 by means of the lugs 16 of the laser cut structure as it is already described above based on FIG. 2*a-c* are conceivable in this connection. However, the following alternative options offer themselves on principle, and there are other versions conceivable, which are not listed below:

- Two pans that are fixed so that they overlap and telescopically move apart radially during retraction (see FIG. 2*b-c*). For example, foils made of Teflon are conceivable.
- Elastic foils can be rolled up or pushed on the stent (retractor/distractor) as a hose. The stent can also be moulded in. Conceivable materials are elastomers such as PU or silicone.
- The characteristics of thermoplastic elastomers can be used to utilise plastic flow properties during retraction. The advantage of this is that the reset forces are reduced as compared to the purely elastic performance.
- By means of a spraying process, a fleece can be created on the stent similarly to vascular implants.
- For the segment-wise separation of the stent (retractor/distractor) 1, marks on the sheath/protective cover 14 are conceivable, which can be detached with a scalpel. In the area of the metal segments 8, ideally perforations are formed on the sheath/protective cover 14, which can be manually detached.

A stent (retractor/distractor) 1 with the following characteristics is proposed according to the invention:

- Single-use stent (retractor/distractor) 1 that can be shaped and adapted any which way.
- Rigid parts 4 of the stent structure are used for connection to fixed points 16.
- The segmental construction enables an individualized cutting to length of stent 1.
- Through the connection to two distraction screws 22, the distraction function can be integrated, e.g. with a cervical application.
- A sheath 14 is used as tissue protection (rigidly overlapping or elastically and/or plastically deformable). Perforations on the sheath 14 can be used for individualized cutting to length.
- Stent 1 can be destroyed for removal (compressing, folding, rolling up . . . )

These characteristics have the following advantages:

- The single-use stent (retractor/distractor) 1 is shapeable and adaptable any which way (plastically or elastically) and so offers advantages for minimally invasive accesses.
- The stent (retractor/distractor) 1 can be used for many accesses on the spinal column (dorsal lumbar, dorsal cervical, ventral cervical) and on the skull.
- Rigid parts 4 of the stent structure are used for connection to fixed points.
- Cost-efficient production of the stent structures with laser and water cutting procedures.
- Transfer of experience from vascular stent production.
- The segmental construction enables individualized cutting to length.
- Retraction can be formed with easy, already known instruments, such as a speculum or a Langenbeck hook.
- Through the connection to two distraction screws 22, the distraction function can be integrated, e.g. with a cervical application.
- The screws 22 also enable an axial fixing of the stent (retractor/distractor) 1.
- A sheath 14 is used as tissue protection (rigidly overlapping or elastically and/or plastically deformable). Perforations on the sheath can be used for individualized cutting to length.
- The planar attachment reduces the access trauma.
- The stent can be destroyed for removal (compressing, folding, rolling up . . . ).

Below, a second preferred exemplary embodiment of the invention is described based on FIGS. 1 to 9, for which the same reference signs for identical elements (of identical construction/function) are used like for the first example of the invention. As for the rest, only those elements/sections of the stent according to the invention are basically described below which differ from the first example/constitute additional features.

In this preferred exemplary embodiment of the invention in hand, the realization of the stent wall according to FIG. 6 shows the two diametrically opposed enlarging sections/elements 2 and the stiffening sections 4 arranged in between in each case the circumferential direction and so also diametrically opposed to each other, like they are also present in the first exemplary embodiment and were already described above. In contrast to the first exemplary embodiment, however, the stiffening sections 4 are composed of axially spaced segments 8 the axial lengths of which are not identical like in the first preferred exemplary embodiment, but which differ from each other in this case.

To be more precise, each stiffening section 2 consists of a number (plural number) of axially short segments 8*a* which are connected to each other in each case by means of axial strips (separable/bendable) in one piece (of material) and at least another long segment 8*b* which is also connected with at least one axially last of the short segments 8*a* by means of axial strips of the same construction/same function.

Like in the first exemplary embodiment, an elastically or plastically stretchable enlarging strip 6 is connected to each short segment (comparable with the segments of the first exemplary embodiment) seen in the circumferential direction, and these strips connect the diametrically opposed short segments of the same axial level with each other (in one piece of material). The diametrically opposed long segments 8*b* of the same axial level are connected with each other by means of a plural number of axially distanced, elastically or plastically stretchable enlarging strips 6, preferably of the same structure and the same size as the strips 6 described above (in a single piece of material). The axial section along the long segments 8*b* of the stiffening sections is constituted by an enlarging section in order to achieve a funnel shape as it is described below based on FIGS. 9 and 10.

As can furthermore be gathered from FIGS. 6 and 7, a number (preferably two) mounting/fixing lugs are moulded on an axial end of the stent. Preferably these have the shape of eyelets and are formed in the stent wall, for example, by means of laser cutting. In this respect, the mounting/fixing lugs first extend level with the stent wall, but can then be bent radially to the inside or outside to the stent wall shaped into a pipe/shaft.

FIGS. 6 and 7 show the segments 8*a*, 8*b* of the stiffening sections 4 as closed plates which are connected with each other into a pipe/shaft by means of the enlarging strips 6 of the enlarging sections 2 in the circumferential direction. Meanwhile, the stiffening sections can be formed with additional functionalities, as it was already described in the first exemplary embodiment as well. Reference is made to FIG. 8 in particular in this connection.

According to that, the segments 8a and/or 8b, but preferably the long segments 8b can be formed axially on the end side with lugs that can be bent radially in each case (according to the first exemplary embodiment of the invention), which are shaped, for example, by laser cutting of the plate-type segments. Furthermore, the segments 8a and/or 8b can have through openings/bores through which wires, strings and/or threads can be pulled. These insertable mounting devices can be used to change the current diameter of the stent pipe or to fix additional elements such as the sealing pans 14 known from the first exemplary embodiment (by means of wiring, clamping or sewing).

In particular, the following functionalities can be arranged individually or in selectable combinations in each case on the segments 8a and/or 8b:

- Lug(s) for the (clamping) fixation of a fluid seal/tissue protection element (cover), for example in the form of foils, vascular implants, shrink-on tubes, etc.,
- Bores for the sewing on of the fluid seal/tissue protection element (cover),
- Bores for wire placement for fixing the fluid seal/tissue protection element (cover),
- Bores for wire or string placement for compression traction mechanisms and/or
- Lugs for fixing on bone screws, in particular pedicle screws (systems), such as the lugs shown in FIG. 8 for so-called "body manipulators".

The functionality of the stent according to the second preferred exemplary embodiment of the invention in hand basically matches the one of the first exemplary embodiment and is explained once more below based on FIGS. 9 and 10.

As can be seen in FIG. 9, the stent according to the invention can axially be enlarged/laced up radially to different degrees at its enlarging sections 2, if necessary. In particular the axial section in the area of the long segments 8b of the stiffening sections/elements 4 is especially suitable for the shaping of a funnel by bending the long segments 8b radially to the outside on their axial free ends, whereby the strips 10 connecting the long segments 8b with the axially closest short segments 8a are bent, as a result of which the stent basically maintains its radial dimension in the area of the short segments 8a.

FIGS. 10a and 10b show a type of application of the stent according to the invention according to the first or second exemplary embodiment.

According to the picture in FIG. 10a, the stent retractor/distractor can be threaded/slid on in combination, for example, with a percutaneous pedicle screw system, by means of a caudally positioned insert sleeve (which is sufficiently known from the state of the art according to the disclosure of the applicant in hand herself and therefore does not need to be described in more detail here), whereby the stent retractor/distractor according to the invention is introduced by means of a dilation system or a guide rod after removal of the insert sleeve for the pedicle screw.

Then the stent retractor/distractor is distally enlarged/spread in the shape of a funnel radially according to FIG. 2b, whereby an access, for example to the spinal disc space, is formed, for example in order to clear out the spinal disc and possibly to insert an inter-vertebral implant for fusion.

The invention claimed is:

1. A stent distractor comprising:
a radially flexibly enlargeable, pipe-shaped sheath, the sheath being divided up in a circumferential direction in at least two sections with different radial flexibility, the at least two sections being formed of one piece of material,
wherein the stent distractor is divided up in an axial direction in a number of segments which are fitted with internal stiffening and enlarging sections in each case,
wherein the segments are connected with each other by axial connecting elements having stiffness, the connecting elements constituting predetermined breaking points for segment-wise length shortening,
wherein the at least two sections comprise at least two stiffening sections,
wherein the stiffening sections are formed or fitted with carrier and/or fixing structures for additional, separate components,
wherein the carrier and/or fixing structures are formed as bow- or eyelet-shaped lugs or tongues, each bow- or eyelet-shaped lug or tongue extending in the axial direction and defining an indentation open in the axial direction in combination with the sheath, and
wherein each stiffening section comprises a plate-shaped wall defining a plurality of circumferential through-slits, each through-slit extending through the wall to form one of said bow- or eyelet-shaped lugs or tongues, said bow- or eyelet-shaped lugs or tongues being selectively bendable through the wall in a radially inward direction or a radially outward direction to attach separate components to the inside or the outside of the stent distractor, respectively,
wherein a two-part sealing foil is provided as an additional component, which is mounted to the bow- or eyelet-shaped lugs or tongues, or the bow- or eyelet-shaped lugs or tongues are pushed in to the foil as the fixing structures and envelopes an outside of the sheath with a loose attachment.

2. A stent distractor comprising:
a radially flexibly enlargeable, pipe-shaped sheath, the sheath being divided up in a circumferential direction in at least two sections with different radial flexibility, the at least two sections being formed of one piece of material,
wherein the at least two sections comprise two stiffening sections and two enlarging sections, the stiffening sections having a greater stiffness than the enlarging sections at least in the circumferential direction,
wherein the stiffening sections are formed or fitted with carrier and/or fixing structures for additional, separate components, the carrier and/or fixing structures each comprising at least two eyelet-shaped lugs that are offset from each other in an axial direction,
the stent distractor further comprising two bone anchoring elements which are provided as additional components formed as nails or distraction screws, which are positioned diametrically to each other, wherein each bone anchoring element is positioned in one of the at least two eyelet-shaped lugs of the corresponding carrier and/or fixing structure in such a way that the bone anchoring elements lie flat against the sheath of the stent distractor on an inside or an outside of the sheath, so that the stent distractor is supported and stabilized across its axial length by the two bone anchoring elements through the eyelet-shaped lugs, and
wherein each stiffening section comprises a plate-shaped wall defining a plurality of circumferential through-slits, each through-slit extending through the wall to form one of said eyelet-shaped lugs, said eyelet-shaped lugs being selectively bendable through the wall in a radially inward direction or a radially outward direction to attach separate components to the inside or the outside of the stent distractor, respectively.

3. The stent distractor according to claim 2, wherein a lacing device formed as a pulling rope is provided as an additional component, which is threaded in the eyelet-shaped lugs in such a way that the stent distractor is radially compressed during a lacing process, with shortening of an active length of the pulling rope.

4. The stent distractor according to claim 2, wherein the enlarging sections each comprise a number of axially spaced, elastic stretching elements which are formed in each case from an accordion wire that extends in the circumferential direction.

5. The stent distractor according to claim 2, wherein the enlarging sections and the stiffening sections are formed by laser or water cutting of a pipe blank.

6. A stent distractor comprising:
a radially flexibly enlargeable, pipe-shaped sheath, the sheath being divided up in a circumferential direction in at least two sections with different radial flexibility, the at least two sections being formed of one piece of material,
wherein the at least two sections comprise two stiffening sections and two enlarging sections, the stiffening sections having a greater stiffness than the enlarging sections at least in the circumferential direction,
wherein the stiffening sections are formed or fitted with carrier and/or fixing structures for additional, separate components, the carrier and/or fixing structures each comprising bow- or eyelet-shaped lugs, wherein a two part sealing foil is provided as an additional, separate component, which is mounted to the bow- or eyelet-shaped lugs, or the bow- or eyelet-shaped lugs are pushed in to the foil as the fixing structures and envelopes an outside of the sheath with a loose attachment, and
wherein each stiffening section comprises a plate-shaped wall defining a plurality of circumferential through-slits, each through-slit extending through the wall to form one of said bow- or eyelet-shaped lugs or tongues, said bow- or eyelet-shaped lugs or tongues being selectively bendable through the wall in a radially inward direction or a radially outward direction to attach separate components to the inside or the outside of the stent distractor, respectively.

7. The stent distractor according to claim 6, wherein a selected number of the bow- or eyelet-shaped lugs are bent radially inward to an inside of the sheath, and a lacing device formed as a pulling rope is provided as a second additional component, which is threaded in the bow- or eyelet-shaped lugs in such a way that the stent distractor is radially compressed during a lacing process, with shortening of an active length of the pulling rope.

8. The stent distractor according to claim 6, wherein the enlarging sections each comprise a number of axially spaced, elastic stretching elements which are formed in each case from an accordion wire that extends in the circumferential direction.

9. The stent distractor according to claim 6, wherein the enlarging sections and the stiffening sections are formed by laser or water cutting of a pipe blank.

10. The stent distractor according to claim 6, wherein the stiffening sections are arranged diametrically opposite to each other, and wherein the enlarging sections are arranged diametrically opposite to each other.

\* \* \* \* \*